United States Patent
Klausman et al.

(10) Patent No.: US 11,806,004 B2
(45) Date of Patent: Nov. 7, 2023

(54) SPRING LOADED TRANSLATING LATERAL RETRACTOR BLADE

(71) Applicant: Astura Medical Inc., Irving, TX (US)

(72) Inventors: Keith Klausman, Irving, TX (US); Joel Gambrell, Irving, TX (US); Thomas Purcell, Irving, TX (US)

(73) Assignee: ASTURA MEDICAL, Irving, TX (US)

( * ) Notice: Subject to any disclaimer, the term of this patent is extended or adjusted under 35 U.S.C. 154(b) by 0 days.

(21) Appl. No.: 17/739,105

(22) Filed: May 7, 2022

(65) Prior Publication Data

US 2022/0354478 A1 Nov. 10, 2022

Related U.S. Application Data

(60) Provisional application No. 63/185,898, filed on May 7, 2021.

(51) Int. Cl.
*A61B 17/02* (2006.01)
*A61B 17/00* (2006.01)

(52) U.S. Cl.
CPC ............... *A61B 17/0206* (2013.01); *A61B 2017/00367* (2013.01)

(58) Field of Classification Search
CPC .............. A61B 17/0206; A61B 17/025; A61B 2017/0256
See application file for complete search history.

(56) References Cited

U.S. PATENT DOCUMENTS

| | | | |
|---|---|---|---|
| 5,554,101 A | | 9/1996 | Matilda et al. |
| 9,113,853 B1* | | 8/2015 | Casey ................ A61B 17/0206 |
| 9,433,405 B2* | | 9/2016 | Ott ..................... A61B 17/0206 |
| 2003/0191372 A1* | | 10/2003 | Dobrovolny ............. F16C 3/28 600/226 |
| 2011/0257487 A1* | | 10/2011 | Thalgott ................ A61B 17/02 600/208 |
| 2017/0231614 A1* | | 8/2017 | Vogel ................... A61B 17/025 600/224 |
| 2019/0110785 A1* | | 4/2019 | Serokosz ........... A61B 17/0206 |
| 2019/0133434 A1 | | 5/2019 | Lee et al. |
| 2019/0216453 A1* | | 7/2019 | Predick ............. A61B 17/0206 |
| 2019/0223854 A1 | | 7/2019 | Baudouin et al. |

FOREIGN PATENT DOCUMENTS

| | | |
|---|---|---|
| CN | 205386160 U | 7/2016 |
| WO | WO2015191836 A1 | 12/2015 |

OTHER PUBLICATIONS

International Search Report and Written Opinion in PCT Application No. PCT/US2022/028231 dated Jul. 26, 2022.

* cited by examiner

*Primary Examiner* — Julianna N Harvey
(74) *Attorney, Agent, or Firm* — Michael R Shevlin

(57) ABSTRACT

A tissue retractor having a spring loaded retractor blade that provides constant downward pressure on the spine to eliminate/reduce tissue from creeping underneath the tips of the blades during use, which decreases operation time and reduces patient risk.

12 Claims, 5 Drawing Sheets

SPRING LOADED TRANSLATING LATERAL RETRACTOR BLADE

CROSS-REFERENCE TO RELATED APPLICATIONS

This application claims the benefit of U.S. Provisional Application No. 63/185,898 filed May 7, 2021, which is incorporated herein by reference.

FIELD

The present invention relates generally to the field of surgery, and more specifically, to a retractor blade for use in Spinal Fusion Surgery.

BACKGROUND

Many types of surgeries require exposure and access through the skin to internal parts of the body ("surgical area"). The opening of the surgical area must be of sufficient size to allow the surgeon ample access for carrying out procedures. The opening should also remain open during the surgery and allow the surgeon to perform the desired procedure.

Retractors are used to perform the required exposure and access through the skin. The retractors are typically mechanized devices having retractor blades designed to generate a pathway through tissue for surgical access. The retractor blades do not automatically adjust to the anatomy to maintain contact with the bony structure (spine) when the retractor blades are opened or toed. This increases the potential to allow tissue creep to occur throughout the operation.

Accordingly, there remains a need for instruments and methods that provide solutions to the problems of current systems. The present invention is directed toward meeting these needs.

SUMMARY

The present invention is directed to a retractor having a spring loaded retractor blade that provides constant downward pressure on the spine to eliminate/reduce tissue from creeping underneath the tips of the blades during use, which decreases operation time and reduces patient risk

DETAILED DESCRIPTION

The present invention is directed to systems, methods, and devices applicable to spinal surgery. More specifically, the present invention is directed to a retractor having a spring loaded retractor blade that provides constant downward pressure on the spine to eliminate/reduce tissue from creeping underneath the tips of the blades during use, which decreases operation time and reduces patient risk.

Figure 1A:
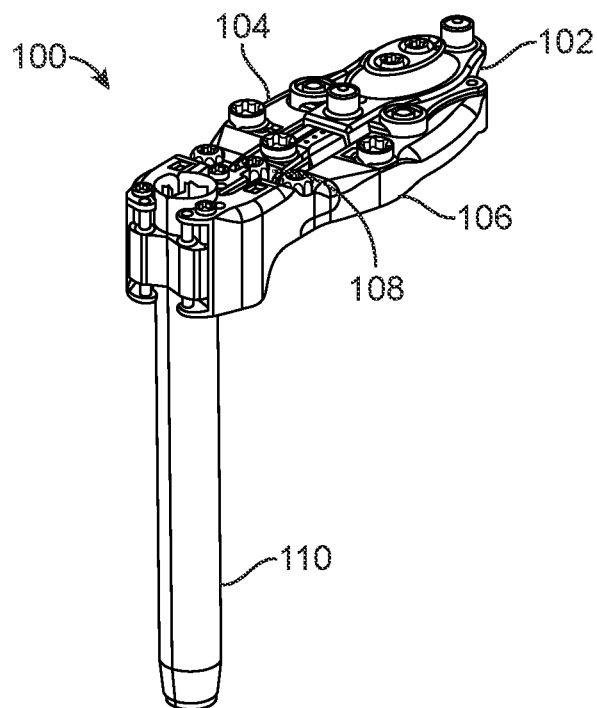
FIG. 1A is a perspective view showing one embodiment of a tissue retractor having spring loaded retractor blades in a closed configuration for delivery through the tissue.
Figure 1B:
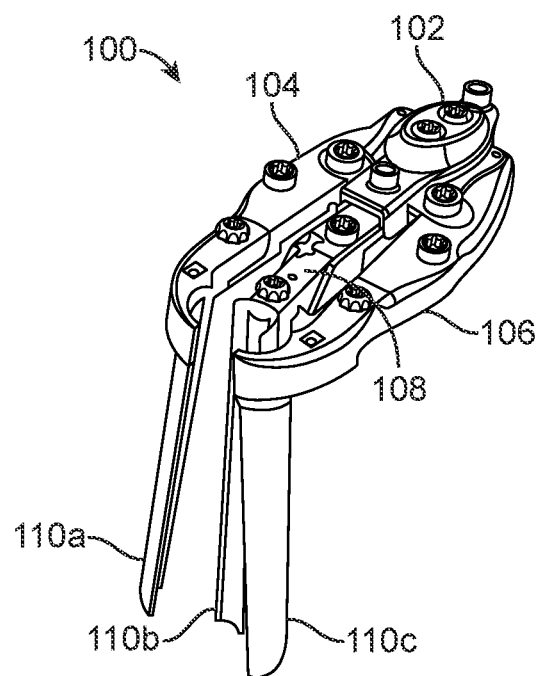
FIG. 1B is a perspective view showing the tissue retractor having spring loaded retractor blades in an open configuration for use.

FIG. 1A is a perspective view showing one embodiment of a tissue retractor 100 having spring loaded retractor blades 110 in a closed configuration for delivery through the tissue. FIG. 1B is a perspective view showing the tissue retractor 100 having spring loaded retractor blades 110 in an open configuration for use.

The tissue retractor 100 includes a central body 102, a right arm 104, a left arm 106 a middle arm 108 and multiple spring loaded retractor blades 110. The spring loaded retractor blades 110 are designed to provide constant downward pressure on the spine to eliminate/reduce tissue from creeping underneath the tips during use, which decreases operation time and reduces patient risk. In the embodiment shown, the multiple spring-loaded retractor blades 110 include a first spring loaded retractor blade 110a coupled to the right arm 104, a second spring loaded retractor blade 110b coupled to the left arm 106, and a third spring loaded retractor blade 110c coupled to the middle arm 108. In other embodiments, there may be more or less spring-loaded retractor blades.

Figure 2:
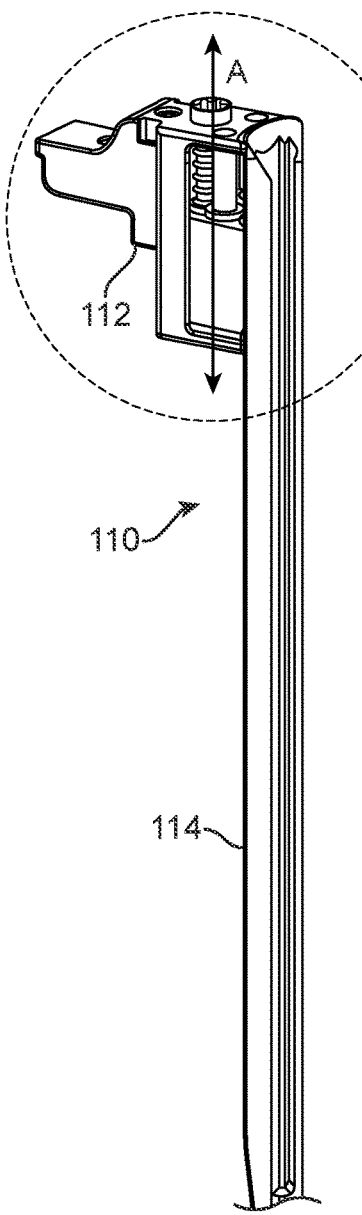
FIG. 2 is a perspective view of the spring loaded retractor blade.
Figure 3:
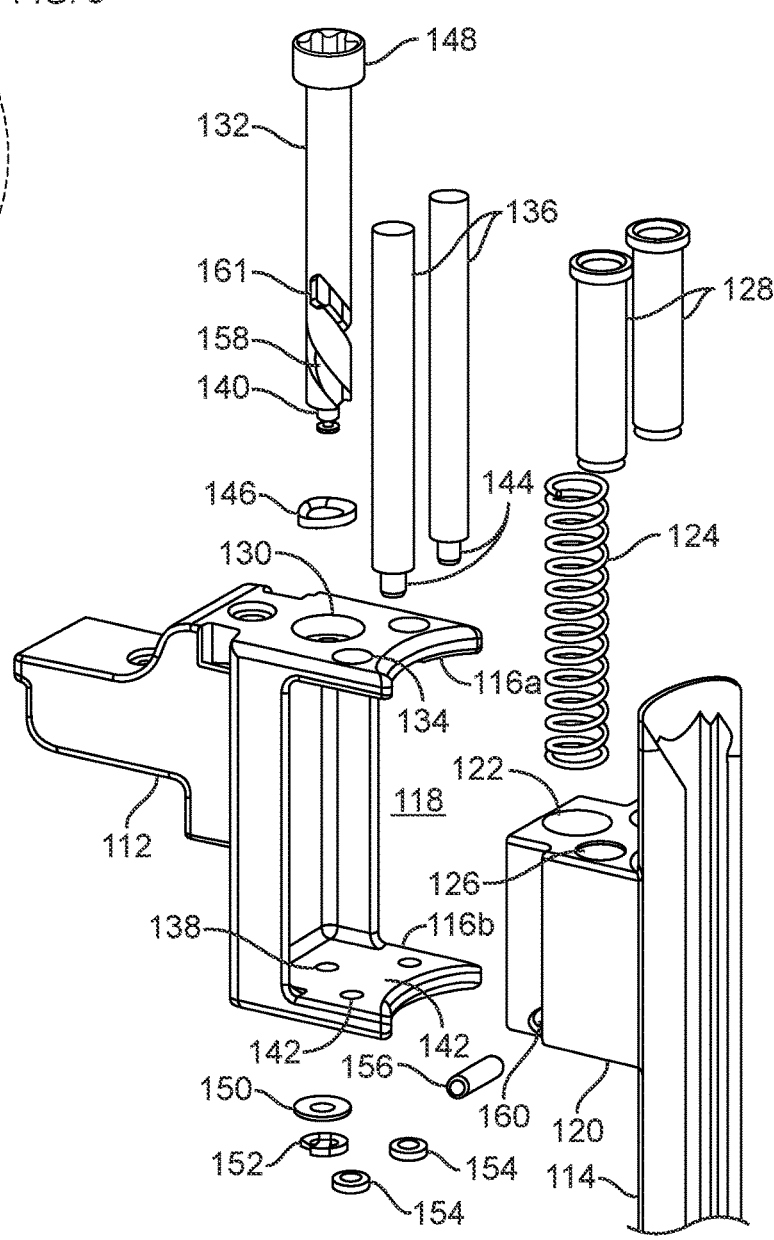
FIG. 3 is an exploded perspective view of a proximal end of the spring loaded retractor blade.

FIG. 2 is a perspective view of the spring loaded retractor blade 110 and FIG. 3 is an exploded perspective view of a proximal end of the spring loaded retractor blade 110. The spring loaded retractor blade 110 includes a body 112 coupled with a translating blade 114. The translating blade 114 is designed to move up or down in relation to the body 112 to allow adjustment of the translating blade 114 to make contact with the spine during a procedure.

The body 112 includes a first end configured to couple with the distal end of the left, right and middle arms 104, 106, 108 of the tissue retractor 100. The body 112 includes a second end having upper and lower blade engagement arms 116a. 116b forming a cavity or recess 118 between them. The translating blade 114 includes an outward extending protrusion 120 configured to fit within the recess 118. The protrusion 120 is smaller than the recess 118 to allow the protrusion 120 to translate in an up/down or axial direction A within the recess 118.

The protrusion 120 is configured to slide on various components within the recess 118 to allow up and down movement of the translating blade 114, including: a spring 124, guide bushings 128, helical bolt 132 and guide pins 136. The protrusion 120 includes multiple holes aligned in the axial direction including a spring hole 122 configured to receive the spring 124 and guide bushing holes 126 configured to receive the guide bushings 128.

The helical bolt 132 is coupled to the upper and lower blade engagement arms 116a. 116b and sized to fit within the spring 124. The helical bolt 132 includes a helical groove 158. A pin 156 is coupled to the protrusion 120 and configured to engage the helical groove 158, such that when the helical bolt 132 is rotated, the pin 156 slides up or down the groove 158 and translates the protrusion 120 up or down, thereby translating the translating blade 114 up or down in relation to the body. The guide pins 136 are coupled to the upper and lower blade engagement arms 116a. 116b, the guide pins 136 being configured to slide within the guide bushing 128 in an up/down or axial direction.

The upper blade engagement arms 116a of the body 112 includes multiple holes including a helical bolt hole 130 configured to receive the helical bolt 132, and guide pin holes 134 configured to receive the guide pins 136. The helical bolt 130 include a helical bolt protrusion 140 on the distal end, and the guide pins 136 include guide pin protrusions 144 on a distal end. The spring 146 is configured to receive the helical bolt 132 and engage a helical bolt head 148 on a proximal end. The spring 146 may be a circular friction spring 146.

The lower blade engagement arms 116b of the body 112 includes multiple holes including a helical bolt protrusion hole 138 configured to receive the helical bolt protrusion 140 and guide pin protrusion holes 142 configured to receive the guide pin protrusions 144.

A washer 150 and retaining clip 152 are configured to engage the helical bolt protrusion 140. End caps 154 are configured to engage the guide pin protrusions 144. The protrusion 120 includes a pin hole 160 configured to receive the pin 156 and engage the helical groove 158 on the helical bolt 132.

Figure 4:
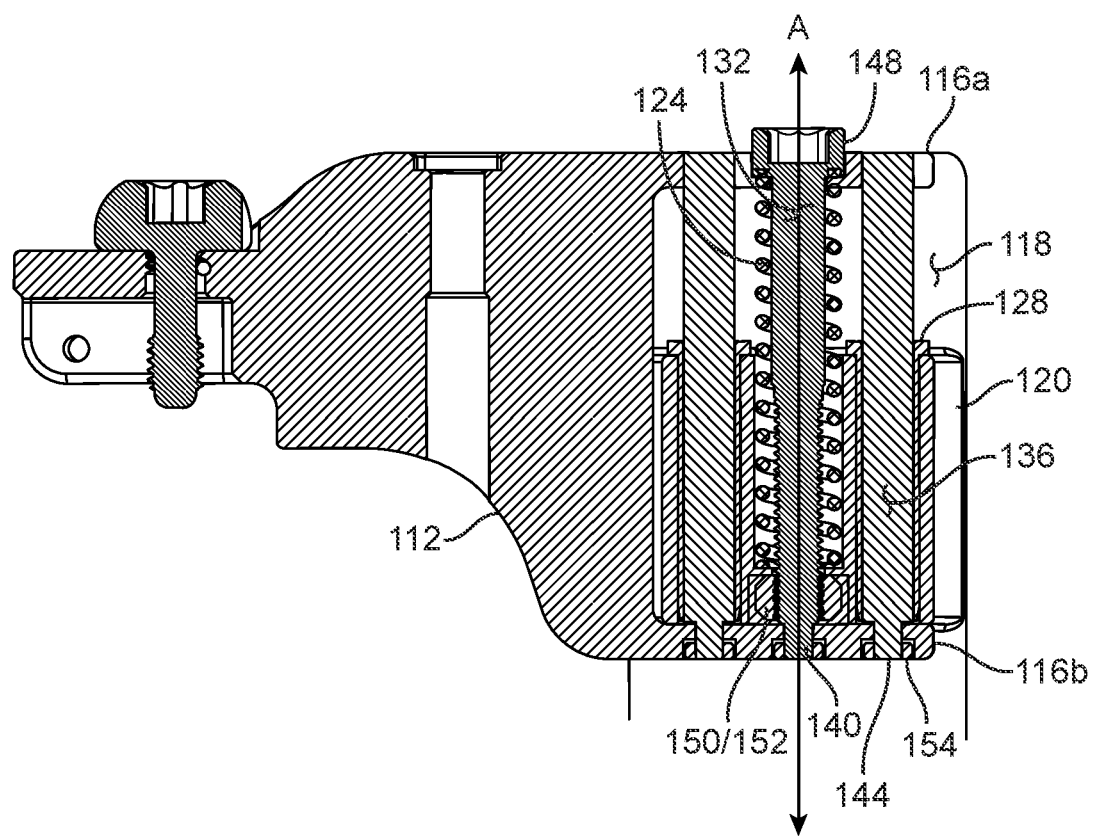
FIG. 4 is a cross sectional view of the proximal end of the spring loaded retractor blade.

FIG. 4 is a cross sectional view of the proximal end of the spring loaded retractor blade 110 showing the components of FIG. 3 in the assembled configuration with the protrusion 120 within the recess 118 of the body 112. Prior to insertion of the protrusion 120, the spring 124 is inserted into the spring hole 122 and the guide bushings 128 are inserted into the guide bushing holes 126.

Once the protrusion 120 is inserted into the recess 118, the helical bolt hole 130 is lined up with the spring 124, and the guide pin holes 134 are lined up with the guide bushing 128. The helical bolt 132 is inserted through the helical bolt hole 130 and the spring 124, with the distal helical bolt protrusion 140 extending through the helical bolt protrusion hole 138. The washer 150 and retaining clip 152 are coupled to the helical bolt protrusion 140 to hold the helical bolt 132 in place while also allowing rotation of the helical bolt 132. The guide pins 136 are inserted through the guide pin hole 134 and guide busing 128, with the distal protrusion 144 extending through the guide pin protrusion holes 142. The guide bushings 128 are configured to slide along the guide pins 136. The end caps 154 are coupled to the guide pin protrusions 144 to hold the guide pins 136 in place.

The pin 156 is inserted in the pin hole 160 and engages the helical groove 158. As the helical bolt 132 is rotated, the pin 156 is configured to slide within the helical groove 160 in an up or down direction and move the protrusion 120 up or down within the recess 118.

Figure 5A:
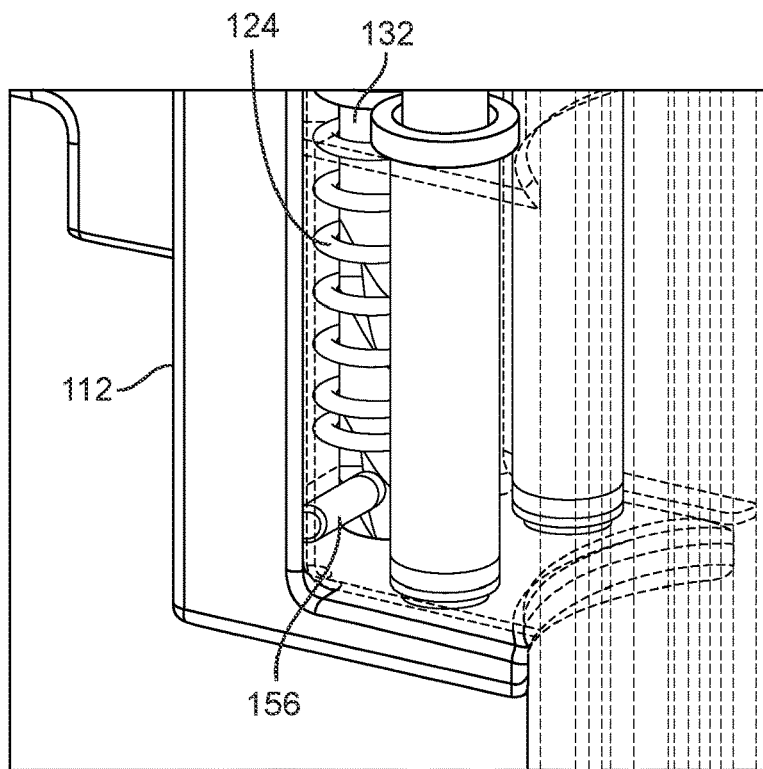
FIGS. 5A and 5B show the engagement of the pin and helical groove.
Figure 5B:
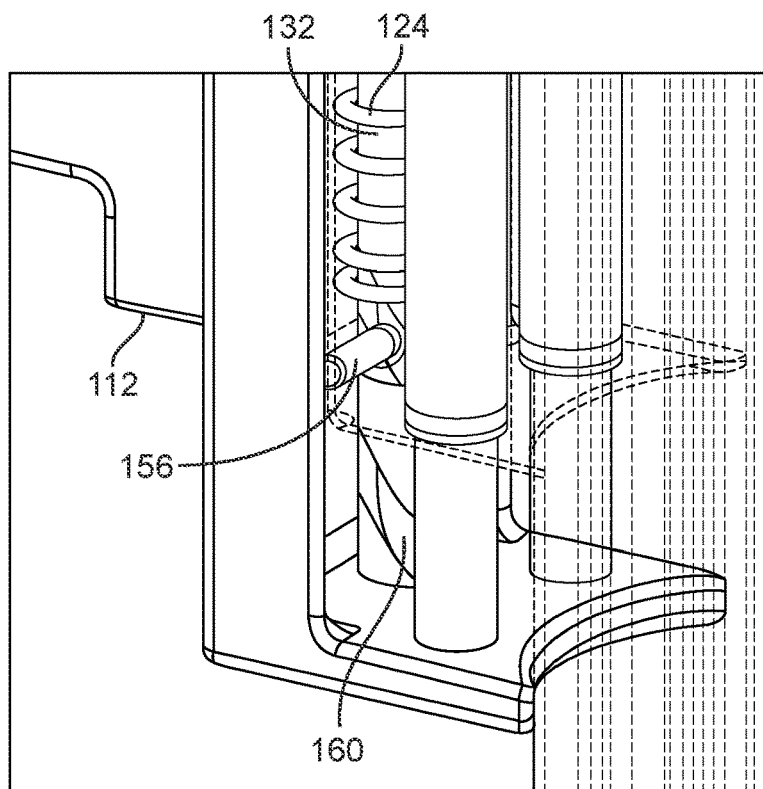

FIGS. 5A and 5B show the engagement of the pin 156 and helical groove 160. In FIG. 5A the protrusion 120 is positioned near the bottom of the recess 118. As the helical screw 132 is rotated, the pin 156 slide up the helical groove 160, translating the protrusion 120 toward the top of the recess 118.

Figures 6A, 6B:
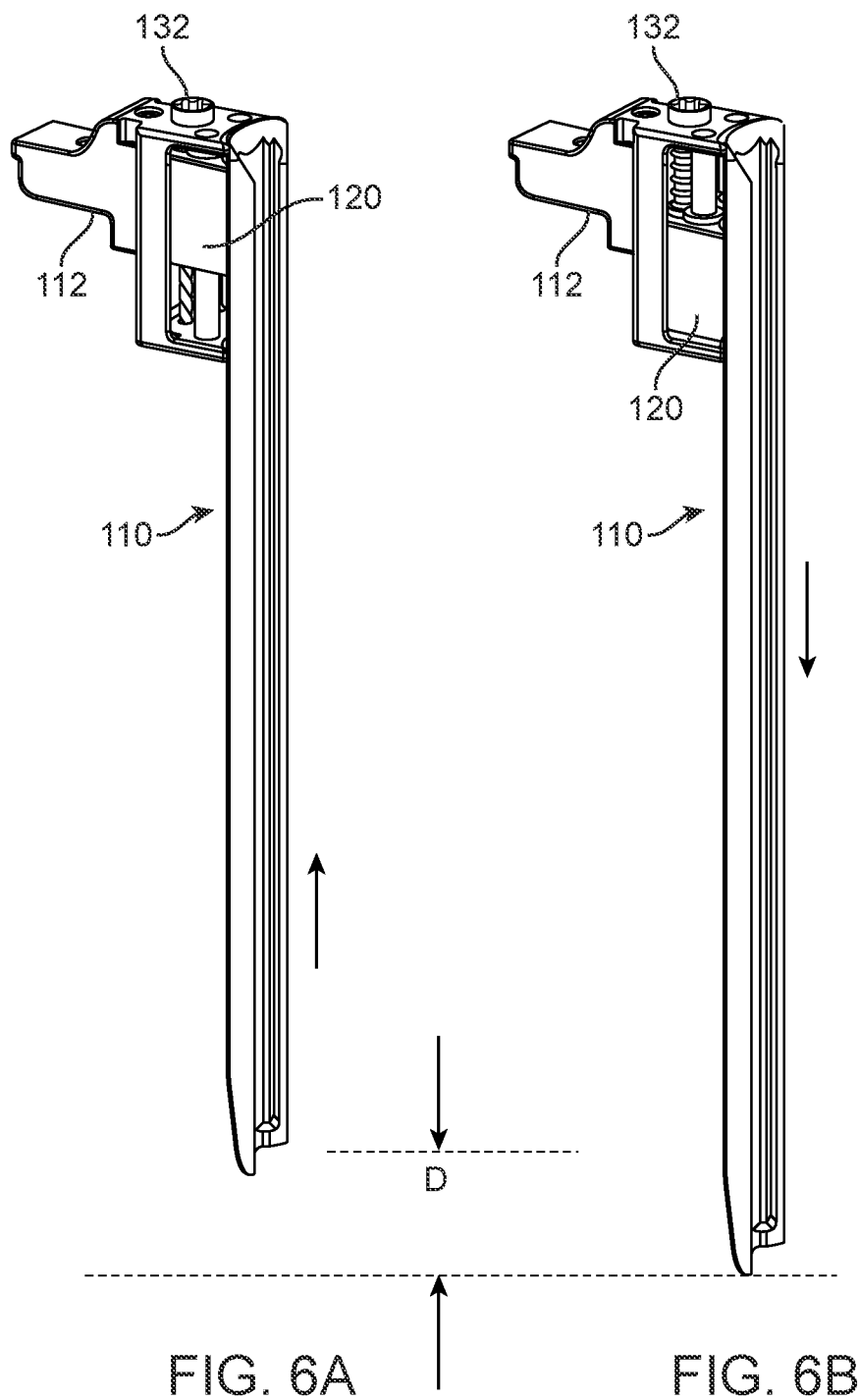
FIG. 6A shows the tissue retractor in a "pre-loaded" delivery configuration with a translating blade protrusion toward the top of the recess.
FIG. 6B shows the spring-loaded retractor blade in the use configuration with the translating blade protrusion toward the bottom of the recess.

FIG. 6A shows the spring loaded retractor blade 110 in a "pre-loaded" delivery configuration with protrusion 120 upward toward the top of the recess 118. The spring loaded retractor blades 110 are designed to be "pre-loaded" by translating the protrusion 120 upward toward the top of the recess via the pin 156 and helical groove 160, which automatically locks it in place by way of the pin 156 engaging a "J" hook feature 161 at the top of the groove 160. "Pre-Loading" is completed prior to placement within the patient.

FIG. 6B shows the spring loaded retractor blade 110 in the use configuration. Once the tissue retractor 100 and spring loaded retractor blades 110 are positioned and secured by a table fixation arm, the spring loaded retractor blades 110 can be released from the "J" hook feature by turning the helical bolt 132 in a clockwise direction so the pin disengages from the "J" hook feature. The J" hook feature which merges with the helical groove 160 on the helical bolt 132 and allows for the spring loaded retractor blades 110 to translate downward at a controllable rate.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A spring-loaded retractor blade comprising:
a body;
a translating blade slidingly coupled to the body, the translating blade being configured to translate up or down in relation to the body;
a spring coupled to the translating blade configured to provide downward pressure on the translating blade;
wherein the body includes a recess and the translating blade includes a protrusion configured to fit within the recess;
wherein the recess is between upper and lower blade engagement arms;
a helical bolt with a helical groove rotatably coupled to the upper and lower blade engagement arms;
the protrusion having a helical bolt hole and a pin hole configured to slidingly receive the helical bolt; and
a pin inserted in the pin hole having one end configured to engage the helical groove;
wherein when the helical bolt is rotated, the pin slides in an up or down direction within the helical groove to move the protrusion in the up or down direction.

2. The spring-loaded retractor blade of claim 1, wherein the helical groove includes a "J" hook feature at the top, the end of the pin being engaged with the "J" hook feature to lock the retractor blade in a "pre-loaded" delivery configuration.

3. The spring-loaded retractor blade of claim 1, wherein the body includes a first end and a second end, wherein the first end is coupled to a retractor arm and the second end is coupled to the translating blade.

4. A spring-loaded retractor blade comprising:
a body;
a translating blade slidingly coupled to the body, the translating blade being configured to translate up or down in relation to the body; and
a spring coupled to the translating blade configured to provide downward pressure on the translating blade;
wherein the body includes a recess and the translating blade includes a protrusion configured to fit within the recess;
wherein the recess is between upper and lower blade engagement arms;

one or more guide pins coupled to the upper and lower blade engagement arms; and one or more guide bushings coupled to the protrusion configured to slidingly receive one or more guide pins;

wherein the protrusion slides in an up or down direction on the guide pins.

5. A spring-loaded retractor blade comprising:
a body having a recess;
a translating blade having a protrusion configured to translate up or down within the recess;
a spring coupled to the translating blade configured to provide downward pressure on the translating blade;
wherein the protrusion includes a spring hole and the spring is positioned in the hole;
wherein the body includes an upper blade engagement arm and a lower blade engagement arm forming the recess between them;
a helical bolt with a helical groove, the helical bolt is rotatably coupled to the upper blade engagement arm and the lower blade engagement arm;
the protrusion having a helical bolt hole configured to slidingly receive the helical bolt and a pin hole; and
a pin inserted in the pin hole having one end extending configured to engage the helical groove;
wherein when the helical bolt is rotated, the pin slides in an up or down direction within the helical groove to move the protrusion in the up or down direction.

6. The spring-loaded retractor blade of claim 5, wherein the protrusion includes a spring hole and the spring is positioned in the hole.

7. The spring-loaded retractor blade of claim 5, wherein the spring loaded retractor blade is configured to be positioned in a "pre-loaded" delivery configuration with the protrusion upward toward the top of the recess by translating the protrusion upward via the pin and helical groove until the pin engages a "J" hook feature at the top of the groove which automatically locks the pin in place.

8. The spring-loaded retractor blade of claim 5, further comprising:
one or more guide pins coupled to the upper and lower blade engagement arms; and
one or more guide bushings coupled to the protrusion configured to slidingly receive one or more guide pins;
wherein the protrusion translates on the guide pins.

9. The spring-loaded retractor blade of claim 5, wherein a first end of the body is coupled to a retractor arm.

10. A tissue retractor comprising:
a retractor body;
two or more retractor arms having a first end coupled to the retractor body and a second end; and
a spring-loaded retractor blade coupled to the second end of the two or more retractor arms comprising:
a body having a first end coupled to one of the two or more retractor arms and a second end;
a translating blade slidingly coupled to the second end of the body being configured to translate up or down in relation to the body; and
a spring coupled to the translating blade configured to provide downward pressure on the translating blade;
wherein the body includes an upper blade engagement arm and a lower blade engagement arm forming the recess between them, and the translating blade includes a protrusion configured to fit within the recess;
a helical bolt with a helical groove rotatably coupled to the upper blade engagement arm and the lower blade engagement arm;
the protrusion having a helical bolt hole configured to slidingly receive the helical bolt and a pin hole; and
a pin inserted in the pin hole having one end extending configured to engage the helical groove;
wherein when the helical bolt is rotated, the pin slides in an up or down direction within the helical groove to move the protrusion in the up or down direction.

11. The tissue retractor of claim 10, wherein the spring loaded retractor blade is configured to be positioned in a "pre-loaded" delivery configuration with protrusion upward toward the top of the recess by translating the protrusion upward via the pin and helical groove until the pin engages a "J" hook feature at the top of the groove which automatically locks the pin in place.

12. A tissue retractor comprising:
a retractor body;
two or more retractor arms having a first end coupled to the retractor body and a second end; and
a spring-loaded retractor blade coupled to the second end of the two or more retractor arms comprising:
a body having a first end coupled to one of the two or more retractor arms and a second end;
a translating blade slidingly coupled to the second end of the body being configured to translate up or down in relation to the body;
a spring coupled to the translating blade configured to provide downward pressure on the translating blade;
one or more guide pins coupled to the upper and lower blade engagement arms; and
one or more guide bushings coupled to a protrusion configured to slidingly receive one or more guide pins;
wherein the protrusion slides in the up or down direction on the guide pins.

* * * * *